(12) United States Patent
Batard et al.

(10) Patent No.: US 9,822,185 B2
(45) Date of Patent: Nov. 21, 2017

(54) USE OF IGG1 IMMUNOGLOBULINS AND/OR LIGANDS OF THE CD32 RECEPTOR FOR TREATING INFLAMMATORY DISEASES AND INCIDENTS VIA THE MUCOSA

(71) Applicant: STALLERGENES SA, Antony (FR)

(72) Inventors: Thierry Batard, Versailles (FR); Philippe Moingeon, Verrieres le Buisson (FR); Laurent Mascarell, Paris (FR); Aline Zimmer, Massy (FR); Emmanuel Nony, Antony (FR)

(73) Assignee: STALLERGENES, Antony (FR)

( * ) Notice: Subject to any disclaimer, the term of this patent is extended or adjusted under 35 U.S.C. 154(b) by 0 days.

(21) Appl. No.: 14/879,331

(22) Filed: Oct. 9, 2015

(65) Prior Publication Data

US 2016/0032018 A1 Feb. 4, 2016

Related U.S. Application Data

(62) Division of application No. 13/319,074, filed as application No. PCT/FR2010/050894 on May 7, 2010, now Pat. No. 9,187,568.

(30) Foreign Application Priority Data

May 7, 2009 (FR) ...................................... 09 53057

(51) Int. Cl.
*A61K 38/00* (2006.01)
*A61K 39/00* (2006.01)
*C07K 16/42* (2006.01)

(52) U.S. Cl.
CPC .... *C07K 16/4291* (2013.01); *A61K 2039/505* (2013.01); *A61K 2039/542* (2013.01);
(Continued)

(58) Field of Classification Search
CPC .................................................. C07K 16/4291
See application file for complete search history.

(56) References Cited

U.S. PATENT DOCUMENTS

| 4,816,567 A | 3/1989 | Cabilly et al. |
| 4,861,719 A | 8/1989 | Miller |

(Continued)

FOREIGN PATENT DOCUMENTS

| EP | 0 173 494 | 3/1986 |
| EP | 0 550 020 | 7/1993 |

(Continued)

OTHER PUBLICATIONS

Schneider et al., (J Autism Dev Discord. 2006. 36:1053-1064).*
(Continued)

*Primary Examiner* — Cherie M Stanfield
(74) *Attorney, Agent, or Firm* — Browdy and Neimark, PLLC

(57) ABSTRACT

The present invention concerns the use of immunoglobulins of $IgG_1$ type, and more generally of ligands of the CD32 receptor, for the treatment of inflammatory diseases and manifestations, in particular of allergies and auto-immune diseases, more particularly the treatment of allergic asthma, the immunoglobulins and ligands being administered via mucosal route, in particular via sublingual route.

4 Claims, 3 Drawing Sheets

Figure 1:
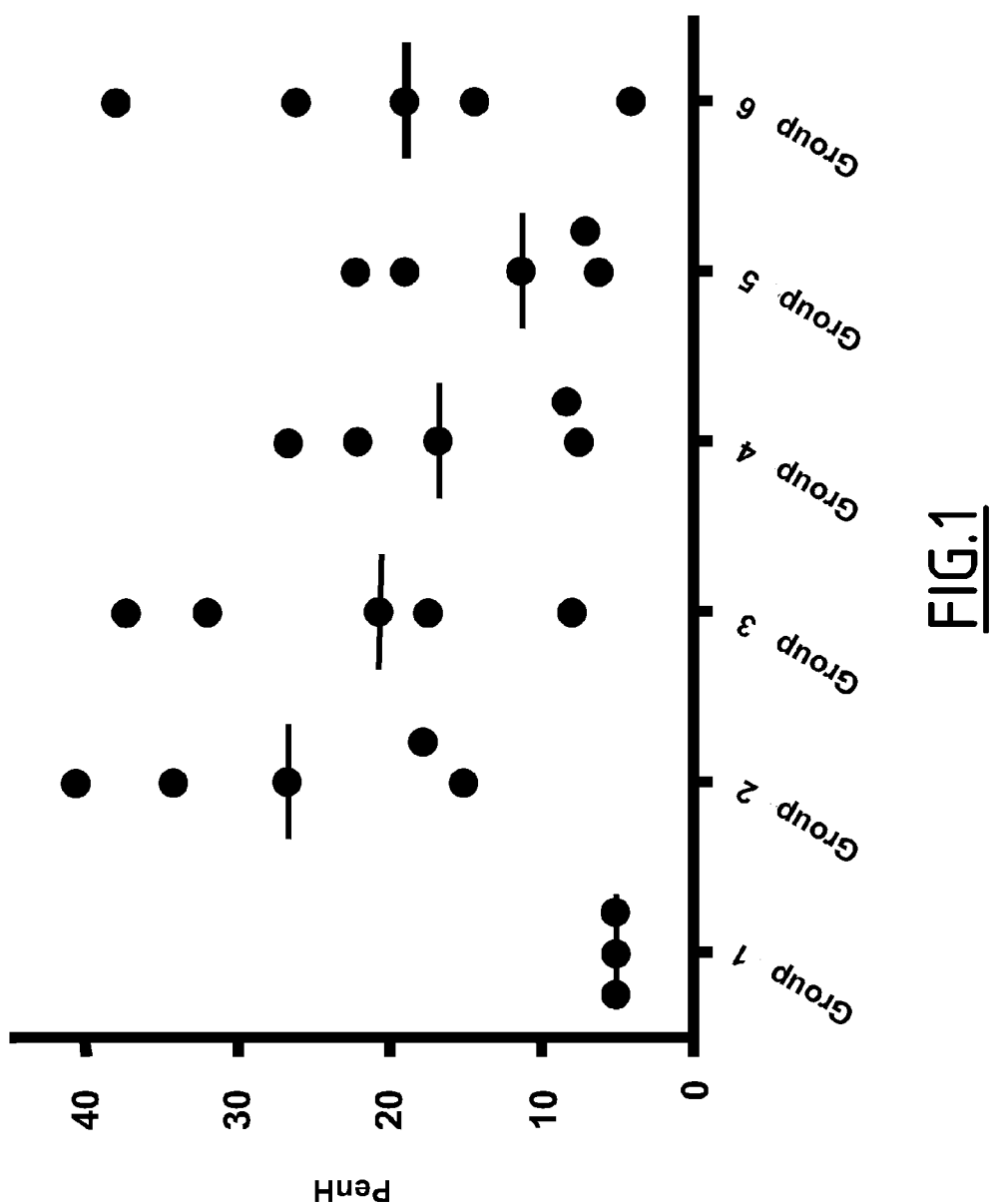

(52) U.S. Cl.
CPC .... *A61K 2039/545* (2013.01); *C07K 2317/41* (2013.01); *C07K 2317/76* (2013.01)

(56) References Cited

U.S. PATENT DOCUMENTS

| | | | |
|---|---|---|---|
| 5,278,056 A | 1/1994 | Bank et al. | |
| 5,585,089 A | 12/1996 | Queen et al. | |
| 5,859,205 A | 1/1999 | Adair et al. | |
| 5,882,877 A | 3/1999 | Gregory et al. | |
| 6,013,516 A | 1/2000 | Verma et al. | |
| 7,744,895 B2 | 6/2010 | Nakao | |
| 8,182,818 B2* | 5/2012 | Fox | C07K 16/241 424/130.1 |
| 9,187,568 B2* | 11/2015 | Batard | C07K 16/4291 |
| 2003/0099635 A1* | 5/2003 | Barstow | A61K 39/395 424/130.1 |
| 2004/0202660 A1* | 10/2004 | Campbell | A61K 35/16 424/145.1 |
| 2007/0048328 A1 | 3/2007 | Nakao | |
| 2007/0135621 A1 | 6/2007 | Bourel et al. | |
| 2008/0206246 A1 | 8/2008 | Ravetch et al. | |

FOREIGN PATENT DOCUMENTS

| | | |
|---|---|---|
| EP | 2000481 A1 | 12/2008 |
| WO | 87/02671 | 5/1987 |
| WO | 94/19478 | 9/1994 |
| WO | 95/14785 | 6/1995 |
| WO | 96/22378 | 7/1996 |
| WO | 98/45322 | 10/1998 |
| WO | 00/50460 A | 8/2000 |
| WO | 02/88317 A | 11/2002 |
| WO | 03/015817 A2 | 2/2003 |
| WO | 03/028668 A2 | 4/2003 |
| WO | 03/041731 A2 | 5/2003 |
| WO | 2004/041867 A1 | 5/2004 |
| WO | 2006/122257 A2 | 11/2006 |
| WO | 2008/057634 A2 | 5/2008 |
| WO | 2008/086395 A2 | 7/2008 |
| WO | 2008/099188 A | 8/2008 |
| WO | 2008/116149 A2 | 9/2008 |
| WO | 2008/123999 A2 | 10/2008 |
| WO | 2009/079382 A1 | 6/2009 |

OTHER PUBLICATIONS

Wigginton, S.J. et al: "An immunoglobulin E-reactive chimeric human immmunoglobin G1 anti—idiotype inhibits basophil degranulation through cross-linking of Fc epsilon RI with Fc gamma RIIb", Clinical and Experimental Allergy 38(2) Abstract—p. 317, right-hand column, last paragraph—p. 318, right—hand column, last paragraph ( 2008).

Rudolf, M.P., et al: "Effect of anti-IgE antibodies on Fc epsilonRI-bound IgE.", Journal of Immunology (Baltimore, MD.: 1950) 157(12):5646-5652 (1950).

Zhou, JosephS., et al: "Mast cell deficiency in Kit(W-sh) mice does not impair antibody—mediated arthritis", Journal of Experimental Medicine, 204(12):2797-2802 (2007).

Saxon A., et al: "Accentuate the negative, eliminate the positive: Engineering allergy therapeutics to block allergic reactivity through negative signaling", Journal of Allergy and Clinical Immunology, Mosby, Inc, US, 121(2): 320-325 (2008).

Sehra, Sarita, et al: "Airway IgG counteracts specific and bystander allergen-triggered pulmonary inflammation by a mechanism dependent on FcgammaR and IFN-gamma." Journal of Immunology, 171(4): 2080-2089 (2003).

Rabinovitch, N. et al: "The role of immunoglobin therapy in allergic diseases", Allergy Icopenhagen), 54(7): 662-668 (1999).

De Groot, AnneS., et al: "Activation of natural regulatory T cells by IgG Fc-derived peptide "Tregitopes"", Blood, 112 (8):3303-3311 (2008).

Robert M. Anthony, et al "Recapitulation of IVIG Anti-Inflammatory Activity with a Recombinant IgG Fe" vol. 320 Apr. 18, 2008, pp. 373-376.

Robert C. Strunk, et al., "Omalizumab for Asthma" The New England Journal of Medicine; 354:2689-95 (2006).

Ravirajan, C.T. et al: "Effect if neutralizing antibodies to IL-10 and C5 on the renal damage caused by a pathogenic human anti-dsDNA antibody", Rheumataology (Oxford), 43(4): 442-447 (2004).

International Search Report—PCT/FR2010/050894—dated Mar. 10, 2011.

Janeway et al., Eds. Immunobiology: The Immune System Health and Disease. 5th Ed. Garland Publishing. New York. pp. 471-490 (2001).

Oralair FDA information.//www.fda.gov/downloads/biologicsbloodvaccines/allergenics/ucm391580.pdf (9 pages). Last accessed Jul. 16, 2014.

\* cited by examiner

US 9,822,185 B2

USE OF IGG1 IMMUNOGLOBULINS AND/OR LIGANDS OF THE CD32 RECEPTOR FOR TREATING INFLAMMATORY DISEASES AND INCIDENTS VIA THE MUCOSA

This application is a division of U.S. application Ser. No. 13/319,074, which is the U.S. National Phase application under 35 U.S.C. §371 of International Application No. PCT/FR2010/050894, filed on May 7, 2010, and claims benefit of priority to French Patent Application No. 0953057, filed on May 7, 2009. The International application was published in French on Nov. 11, 2010 as WO 20101128265 A2 under PCT Article 21(2). All of these applications are hereby incorporated herein by reference.

The present invention concerns the use of type $IgG_1$ immunoglobulins and more generally of ligands of the CD32 receptor, for the treatment of inflammatory diseases and manifestations, in particular allergies and autoimmune diseases, and more particularly for treating allergic asthma, the immunoglobulins and the ligands being administered via mucosal route, in particular via sublingual route.

The present invention also concerns the use of anti-IgE antibodies, more particularly anti-IgE $IgG_1$ antibodies particularly having the capacity to bind IgEs on the surface of mastocytes or basophiles without dissociating said IgEs from their receptors, for the treatment of inflammatory diseases and manifestations, notably IgE-related pathologies such as immediate allergies or type 1 hypersensitivities, some mastocytoses or allergic manifestations associated with parasitoses. Anti-IgE antibodies are in particular antibodies bridging IgEs fixed to the receptors on the surface of mastocytes or basophiles.

Allergies are abnormal hypersensitivity reactions, non-adapted and excessive of the organism, subsequent to contact with an element, most often external, the allergen. These reactions are divided into four groups according to the mechanisms of these reactions leading to the allergic symptoms. Immediate allergy or type 1 hypersensitivity is characterized by the release by the mastocytes and basophiles of pro-inflammatory mediators including histamine, pro-inflammatory cytokines and leukotrienes (Mobs et al. (2008) *Int. Arch. Allergy Immunol.* 147: 171-178) following a stimulation induced by IgE bridging on the surface of these cells.

The onset of type 1 hypersensitivity is the result of a series of events involving different actors of the immune system. An allergen will first be taken in charge by antigen presenting cells and B lymphocytes specific to the allergen. Fragments of this allergen will then be presented via the major histocompatibility complex, or MHC, to T lymphocytes leading to activation of the T lymphocytes specific to the antigen and to the secretion of IL-4 by the latter. The activation of B lymphocytes by these T lymphocytes in the presence of IL-4 and the allergen will induce the differentiation of these B lymphocytes into plasmocytes secreting IgE that are specific to the allergen. The IgEs thus produced will bind to the surface of the mastocytes and basophiles via their Fc end. At the time of a second contact, the allergen will bridge these IgEs and induce the release of pro-inflammatory substances by the basophiles and mastocytes, particularly via a degranulation phenomenon (Bush et al. (2004) *Treat. Respir. Med.* 3: 45-57; Strunck et al. (2006) *N. Engl. J. Med.* 354: 2689-2695). These substances are responsible for allergy symptoms such as asthma, rhinitis or conjunctivitis.

IgEs are known to be capable of fixing themselves via their Fc part to two types of receptors, the high affinity RFcεI receptor and the low affinity RFcεII or CD23 receptor (Klubal et al. (1997) *J. Invest. Dermatol.* 108: 336-342, Dierks et al. (1993) *J. Immunol.* 150: 2372-2382), the mastocytes and basophiles strongly expressing RFcεI.

The use of different immunoglobulins has been envisaged for the treatment of inflammatory diseases and allergies.

For example, Nimmerjahn and Ravetch reported that intravenous Igs (IVIG) administered at high doses allowed the treatment of autoimmune and inflammatory diseases (Nimmerjahn and Ravetch (2007) *JEM* 204:11-15). According to the authors, the anti-inflammatory effect observed with IVIGs is related to an IgG population carrying sialic acids at the glycans N-linked to the Asn297 residue of the Fc region of these IgGs. More precisely, this anti-inflammatory activity is dependent upon sialylation by 2,6 bonds of the next-to-last galactose of the N-glycosylation chain linked to the Asn297 residue (Anthony et al. (2008) *Science* 320:373-376). In this latter publication, it is proposed to administer IVIGs via intravenous route to treat inflammatory diseases.

International application WO 2008/057634 proposes the use of a polypeptide comprising at least one IgG Fc region having a sialylation level higher than that of a non-purified antibody preparation to treat in inflammatory disease. In this type of strategy, the sialylation of the IgGs is shown to be particularly important to obtain a better efficacy in the treatment of the inflammatory disease.

International application WO 2009/079382 also describes the use of a polypeptide comprising at least one IgG Fc region having a higher sialylation level than that of a non-purified antibody preparation for the treatment of inflammatory diseases. Here again, the sialylation of IgGs is necessary to observe an anti-inflammatory activity. Three distinct IgG states have been indeed defined depending on the level of sialylation of their Fc region (Anthony et al. (2008) *Science* 320:373-376). In its desilylated state, IgGs would impart cytotoxic activity by binding to activator Fc receptors. IgGs would lose their cytotoxic activity by sialylation of the Fc linked glycan, thereby converting the IgGs to a non-reactive, non-inflammatory state by reducing the binding with the FcR receptor. Finally, IgGs would become anti-inflammatory by binding of the 2,6 sialic acid with the corresponding receptor. It has more precisely been shown that the anti-inflammatory effect of these IVIGs in sialylated form was due to their binding to the SIGN-R1 receptor, corresponding to the human DC-SIGN receptor (Anthony et al. (2008) *Proc. Natl. Acad. Science* 105:19571-19578). The SIGN-R1 receptor is located in the mouse on the macrophages of the marginal region of the spleen, whilst its human DC-SIGN homologue is present in the dendritic cells.

To obtain an optimal anti-inflammatory effect, it therefore appears necessary that the SIGN-R1/DC-SIGN receptors should be directly accessible to the administered immunoglobulins. Yet, the present inventors have shown that these receptors were only found at tongue level in the muscle tissue far from the site of administration when administering via sublingual route. Therefore, the use of IVIGs is not suitable for the treatment of inflammatory diseases via mucosal route.

Surprisingly, the inventors have observed an improvement in the symptoms of allergic asthma by administering $IgG_1$ type antibodies via sublingual route, whether or not in sialylated form, without such improvement being related to any particular idiotype. In parallel they have evidenced that the tissues of human gums comprise a greater proportion of CD32 receptors than of CD16 activator receptors, in particular at the papillary corium. Without wishing to be bound by any mechanism of action, the anti-inflammatory effect observed with antibodies of IgG$_1$ type (of which some are not sialylated) administered via sublingual route could be mediated by their binding to CD32 receptors.

Additionally, a strategy for allergy therapy described in the prior art consists of specifically targeting IgEs.

The depletion of IgE-secreting B lymphocytes has therefore been envisaged. In patent application WO2008116149, anti-IgE antibodies, capable of recognizing particular epitopes of surface IgEs of B lymphocytes have been developed. These antibodies will lead to the bridging of surface IgEs and, in the absence of other signals, will induce apoptosis of B lymphocytes. These anti-IgE antibodies have as other particularity the fact that they do not recognize IgEs on the surface of basophiles and mastocytes, in order to avoid the bridging of these antibodies on the surface of these cells, a bridging which would lead to the release of pro-inflammatory substances.

Other research has also endeavoured to avoid the clinical manifestations of allergy by preventing the binding of IgEs onto the surface of basophiles and mastocytes.

For example, a human anti-IgE antibody IgG1κ type humanised at 95% has been developed and used in therapy under the name Omalizumab, marketed under the trade name Xolair (Genentech/Novartis). This antibody was produced so as to have two essential characteristics. First it inhibits the binding of IgEs to the RFcεl receptors found on the surface of mastocytes and basophiles, by binding to an epitope of the circulating IgE molecule involved in this binding (Presta et al. (1993) *J. Immunol.* 151: 2623-2632). This antibody is then and subsequently incapable of recognizing the IgE antibodies fixed to the basophiles or mastocytes, the fixing site being masked. This latter characteristic appeared to be essential to avoid activation of these cells which would take place if the anti-IgE was capable of recognizing surface IgEs and therefore of to bridging them in the same manner as an allergen.

The use of such an anybody allowed the intensity of allergy symptoms to be reduced by sequestering and leading to the elimination of circulating IgEs which, via retro-control, induces a drop in the number of RFcεl receptors on the mastocytes of basophiles (Bush et al. (2004) *Treat. Respir. Med.* 3: 45-57, Saini et al. (1999) *J. Immunol.* 162: 5624-5630). The indication for Omalizumab remains limited however to the treatment of adolescents (aged 12 or more) and to adults suffering from moderate to severe persistent asthma who also present with a positive skin test or in vitro reactivity to a perennial aero-allergen and in whom treatment with inhaled corticoids does not enable controlling this asthma (Bang et al. (2004) *BioDrugs* 18: 415-418). This limited use is particularly due to a certain number of side effects and defects of Omalizumab, and to the lack of information on the long-term effect of Omalizumab. Among the side effects, particular mention may be made of local reactions at the injection site (Omalizumab: new drug (2007) *Prescrire Int.* 16: 179-182), the re-onset of nasal polyposis (Tonnel et al. (2006) *N. Engl. J. Med.* 355: 1282), subacute adrenal insufficiency (Tonnel et al. (2006) *N. Engl. J. Med.* 355:1282), and the possible inducing of Churg and Strauss syndrome (Winchester et al. (2006) *N. Engl. J. Med.* 355: 1281-1282). Anaphylaxis reactions are also observed (Omalizumab: new drug (2007) *Prescrire Int.* 16: 179-182), which means that the product must compulsorily be administered under strict medical supervision. In addition, the patient must see a doctor every two to four weeks for one to three subcutaneous injections of the product. The treatment must theoretically be taken all one's life insofar as the effects leading to improvement in symptoms (decrease in circulating IgEs and drop in the number of receptors on the surface of the basophiles) are reversible when treatment is stopped (Saini et al. (1999) *J. Immunol.* 162: 5624-5630).

It can also be envisaged that the elimination of more than 95% of circulating IgEs may become problematic insofar as IgEs may play a role in the fight against parasitosis (Cooper et al. (2008) *Allergy* 63: 409-417) and/or against cancers (Gould et al. (1999) *Eur. J. Immunol.* 29: 3527-3537, Karagiannis et al. (2003) *Eur. J. Immunol.* 33: 1030-1040, Karagiannis et al. (2007) *J. Immunol.* 179: 2832-2843, Karagiannis et al. (2008) *Cancer Immunol. Immunother.* 57: 247-263). Clinical studies have effectively shown that patients treated with Omalizumab have an increased probability of contracting cancers of various types (0.5%), compared with patients under placebo (0.2%).

Finally, treatment with Omalizumab may prove to be costly.

In order to reduce the quantities of anti-IgE antibodies administered throughout treatment, improved antibodies directed against the IgEs having very strong affinity for the latter have been described. For example, patent application EP2000481 has described anti-IgE antibodies blocking the binding of IgEs to their high affinity RFcεl receptor for use in therapy and for allergy diagnosis.

In application WO2008123999, the anti-IgE antibodies used are human antibodies, which allow avoidance of the risk of an immune reaction against humanised murine antibodies.

Application EP0550020 describes antibodies capable of recognizing IgEs fixed to the surface of mastocytes and basophiles and of dissociating them from their receptors on the surface of these cells. Therefore, these antibodies do not induce the bridging of IgEs and hence the release of pro-inflammatory mediators.

All these studies on anti-IgE antibodies as vectors for the treatment of immediate allergies are in agreement on the fact that said anti-IgE antibodies must necessarily be incapable of bridging IgEs on the surface of the mastocytes and basophiles, in order to avoid the release of pro-inflammatory mediators induced by this bridging. In addition, some of these studies, even all these studies, arrive at eliminating all circulating IgEs which, as mentioned previously, may lead to uncomfortable side effects.

Current methods for treating allergies using anti-IgE antibodies are therefore unsatisfactory having regard to the above-mentioned disadvantages.

The inventors have henceforth shown that an immunoglobulin of IgG$_1$ type, in particular anti-IgE, and in particular an anti-IgE IgG1 having the capacity to bridge IgEs on the surface of mastocytes and basophiles, surprisingly induces an improvement in the symptoms of allergic asthma when administered via sublingual route.

Definitions

The terms "antibody" and "immunoglobulin" have the same meaning and are used indifferently in the present application. An antibody corresponds to an immunoglobulin and to the immunologically active portions of immunoglobulins, these being molecules which contain the specific binding sites of a given antigen.

The term antibody covers the whole antibody but also fragments of the antibody and variants of the antibody including derivatives such as humanised antibodies. In natural antibodies, two heavy chains are bonded to each other via disulfide bridges and each heavy chain is bonded to a light chain also via a disulfide bridge. There exists two types of light chains, the lambda chains (λ) and kappa (κ) chains. There are five main classes of heavy chains which determine the functional activity of the antibody: IgM, IgD, IgG, IgA and IgE. Each chain contains distinct domains. The light chain contains two regions, a variable region (VL) and a constant region (CL). The heavy chain contains four or five regions according to class of antibody: a variable region (VH) and three to four constant regions (CH1, CH2, CH3 and optionally CH4, grouped together under the denomination CH). The variable regions of each of the light chains (VL) and heavy chains (VH) determine the specificity for the antigen and the fixing site on this antigen.

The constant regions of the light chains (CL) and heavy chains (CH) impart major biological properties to the antibody such as the associating of antibody chains together, mobility through the placenta, the fixing of complement and/or the fixing to Fc receptors (FcR). The Fv fragment corresponds to the N-terminal part of the Fab fragment, described below, of the immunoglobulin and comprises the variable portions of a light chain and of a heavy chain (VL and VH). The specificity of the antibody lies in the structural complementarity between the recognition site of the antibody and the antigenic determinant. The recognition site of the antibody essentially consists of residues derived from hypervariable regions or complementarity determining regions (CDRs). Occasionally, the residues derived from non-hypervariable regions or from framework regions (FRs) influence the general structure of the region and hence the recognition sites. The term "complementarity determining regions" (CDR) relates to sequences of amino acids which together define the affinity of the fixing and specificity of the natural Fv region for the fixation site of a native immunoglobulin.

Each of the light chains and each of the heavy chains of an immunoglobulin has three CDRs designated L-CDR1, L-CDR2, L-CDR3 and H-CDR1, H-CDR2, H-CDR3, respectively. The fixing site of the antigen therefore includes these six CDRs, comprising the CDRs of each of the heavy and light chains of a variable region.

The framework regions (FRs) correspond to the sequences of amino acids located between the CDRs i.e. portions of the variable regions of the immunoglobulin light and heavy chains which are relatively conserved between different immunoglobulins of one same species (Kabat et al. (1991) National Institutes of Health, Bethesda, Md.). The term "human framework region" is used to designate a framework region which is essentially identical (about 85%, preferably 90%, 95% or 100%) to the framework region of a natural human antibody.

As is well known to persons skilled in the art, four sub-classes can be distinguished among the antibodies of IgG type: $IgG_1$, $IgG_2$, $IgG_3$ and $IgG_4$. These sub-classes differ in the constant regions of their chains γ ($γ_1$ to $γ_4$). While there is no less than 95% sequence identity between the domains, the hinge regions are notably different which determines diverse physicochemical behaviour and effector properties.

The term "monoclonal antibody" or "mAb" (for <<monoclonal Antibody>>) designates an antibody having a unique amino acid composition which is directed against a specific antigen and which can be produced by a single clone of B cells, or hybridoma. Monoclonal antibodies can also be recombinant i.e. be produced by protein engineering techniques.

The term "anti-idiotypic antibody" designates an antibody directed against antigenic determinants present on the variable regions of another immunoglobulin, either at the CDRs or outside.

The term "chimeric antibody" designates a recombinant antibody which comprises a VH region and a VL region of an antibody derived from a non-human animal, in association with a CH region and a CL region of another antibody, in particular of a human antibody. The non-human animal may be a mouse, a rat, a rabbit, a hamster etc. The term "chimeric antibody" may also be used to describe a multispecific antibody i.e., specific to at least two different antigens.

The term "humanised antibody" means a human antibody (acceptor antibody) in which the complementarity regions (CDRs) are replaced by CDR regions forming the binding site to the antigen and originating from a donor antibody specific to the antigen. Optionally, the acceptor human antibody, in addition to the CDR regions, receives amino acids from the framework region of the donor antibody.

The term "antibody fragment" is used for a portion of an intact antibody, preferably the antigen fixing region the variable region of the intact antibody. As an example of antibody fragments, mention may be made of the fragments Fab, $F(ab')_2$, Fab', $ds(Fv)_2$, $sc(Fv)_2$, Fc, the diabodies (such as described below) and the multispecific antibodies able to be obtained from antibody fragments.

The term "Fab" designates an antibody fragment having a molecular weight of about 50,000 daltons and an antigen fixation. These fragments are composed of about one half of the N-terminal part of the heavy chain and the entirety of the light chain which are linked by a disulfide bridge. These fragments can be obtained by treating the immunoglobulin with a protease, the papain.

The term "$F(ab')_2$" means an antibody fragment having a molecular weight of about 100.000 daltons and antigen fixation activity. This fragment is slightly larger than the two Fab fragments linked by a disulfide bridge in the hinge region. These fragments are obtained by treating an immunoglobulin with a protease, the pepsin. The Fab fragment can be obtained from the $F(ab')_2$ fragment by cleaving the disulfide bridge of the hinge region.

A single Fv chain (scFV) corresponds to a heterodimer VH-VL that is covalently linked. This Fv chain is frequently the result of the expression of a fusion gene including the genes encoding VH and VL bonded by a linker sequence coding for a peptide. The human scFv fragment may include CDRs regions which are held in a suitable conformation, preferably through the use of genetic recombination techniques. The "dsFv" fragment is a VH-VL heterodimer stabilized by a disulfide bridge; it may be divalent ($dsFV_2$). Fragments of divalent antibodies $sc(FV)_2$ or multivalent antibodies may be formed spontaneously by association of monovalent scFvs or may be produced by linking scFv fragments with peptide linkers.

The Fc fragment is the support for the biological properties of the antibody, in particular its capacity to be recognized by immunity effectors, or to activate complement. It is constituted of constant fragments of the heavy chains (CH2) beyond the hinge region.

The term "diabodies" means small antibody fragments having two antigen fixation sites. These fragments, in the same polypeptide VH-VL chain, comprise a variable region of the heavy chain VH connected to a variable region of the light chain VL. By using a linker sequence which is too short to allow pairing of two regions of the same chain, the pairing with two complementary regions of another chain necessarily occurs and thereby two antigen fixation sites are created.

IgG$_1$ and Ligands of the CD32 Receptor

The invention concerns an immunoglobulin of IgG$_1$ type for use in the treatment of inflammatory diseases and manifestations, in particular of allergy or autoimmune disease, the immunoglobulin being administered via mucosal route in particular via sublingual route.

The inflammatory disease or manifestation may also be a mastocytosis, particularly a mastocytosis induced by anaphylactic shock, or a parasitosis.

The immunoglobulins of IgG$_1$ type and the ligands of the CD32 receptor according to the invention may in particular be found in or be in the form of an intravenous immunoglobulin composition also called IgIV or IVIG.

As is well known to those skilled in the art, intravenous immunoglobulins are therapeutic preparations of normal human IgGs obtained from a mixture of plasmas derived from more than 1000 healthy individuals. They are generally and almost exclusively intact IgGs with a half-life of 3 to 4 weeks, with distributions into subclasses similar to those observed in normal human serum. IVIGs typically contain less than 5% IgG aggregates, from 0 to 7% of IgG F(ab')$_2$ fragments and, depending on commercial preparations, from 0.06 to 40 mg of IgA per gram of proteins. The IgGs included in IVIGs have a broad spectrum of reactivity and are therefore directed against exogenous antigens, autoantigens and antibodies.

The inventors, having also evidenced a strong density of CD32 receptors at the papillary corium which corresponds to the area in which the immunoglobulins and proteins generally diffuse when administered via sublingual route, drew the conclusion therefrom that any CD32 ligand could be used via sublingual route to induce the treatment of inflammatory diseases and manifestations. More generally, any CD32 ligand can be used via mucosal route to treat inflammatory diseases and manifestations insofar as this mucosa has a strong density of CD32 receptors.

The invention therefore also concerns a ligand of the CD32 receptor, preferably a ligand of the CD32B receptor, in particular an IgG$_1$, for use in the treatment of an inflammatory disease or manifestation, of an allergy or autoimmune disease, the ligand being administered via mucosal route in particular via sublingual route.

Within the context of the invention, the terms "CD32 receptor" and "FcγRII receptor" are used indifferently and refer to a surface receptor protein present on most immune cells and which binds to the Fc fragment of immunoglobulins. As is well known to those skilled in the art, the CD32 receptors comprise a group of receptors including the isoforms CD32A, CD32B and CD32C, all having two extracellular regions. CD32A is expressed on monocytes, macrophages, neutrophils and platelets. CD32C is expressed on NK cells. CD32B finally, which includes two isoforms CD32B1 and CD32B2, is expressed on B lymphocytes, basophiles, mastocytes, monocytes, macrophages and dendritic cells.

CD32A initiates endocytosis, phagocytosis, antibody-dependent cell cytotoxicity and the release of inflammation mediators. CD32B transduces inhibitor signals which downregulate the immune functions triggered by the activator receptors. In particular, CD32B inhibits the activation of mastocytes, basophiles, B lymphocytes and T lymphocytes. It is composed of 2 extracellular regions of Ig type which bind the Fc region of IgGs, a transmembrane region and an intracytoplasmic tail with an inhibitor motif based on the phosphotyrosine of the immune receptor (ITIM). The activation of CD32B leads to the recruitment of phosphatases at the ITIM motif which inhibit activation of the signal coming from other activator receptors.

Preferably the CD32 receptor of the invention corresponds to the CD32B isoform.

By "ligand of the CD32 receptor" is meant herein molecules binding specifically to the CD32 receptor and preferably inducing the signal mediated by CD32.

Techniques allowing identification of the ligands of the CD32 receptor, in particular ligands of the CD32B receptor are well known to those skilled in the art. They particularly include the techniques comprising:

a) contacting the candidate ligand with (i) a recombinant CD32 receptor, in particular a CD32B receptor, or a peptide derived from the CD32 receptor in particular from the CD32B receptor; or with (ii) an indicator cell derived from cell lines expressing CD32, in particular CD32B, on their surface; and b) determining the inducing of the signal mediated by CD32, in particular by CD32B.

The indicator cells may be CD32 positive IIA1.6 cells for example (Van den Herik-Oudijk et al. (1995) *Blood.* 85:2202-11).

The determination of the inducing of the signal mediated by CD32, in particular mediated by CD32B, may consist for example in determining the phosphorylation profile of the ITIM motif of the CD32 receptor, in particular of the CD32B receptor, after contacting with the candidate ligand. It may also comprise inhibition tests of calcium mobilisation and/or inhibition tests of the secretion of cytokines such as IL-2.

Therefore candidate ligands inducing dephosphorylation of the ITIM motif of the CD32 receptor, in particular of the CD32B receptor, and/or inhibiting calcium mobilisation and/or inhibiting IL-2 secretion can be considered as ligands of the CD32 receptor, in particular as ligands of the CD32B receptor.

Examples of techniques for identifying ligands of the CD32 receptor are also described for example in American application US2007/0135621.

Preferably the ligand of the CD32 receptor, in particular the ligand of the CD32B receptor of the invention is an immunoglobulin.

The immunoglobulins which bind the CD32 receptors in particular the CD32B receptors, are well known to those skilled in the art and particularly include IgG$_1$, IgG$_4$, IgG$_3$ and IgG$_2$.

In particular, the ligands of the CD32 receptor according to the invention can be intravenous immunoglobulins also called IgIVs or IVIGs.

In a particular embodiment, the ligand of the CD32 receptor according to the invention is an IgG$_1$.

A ligand of the CD32 receptor or an immunoglobulin of IgG$_1$ type according to the invention may in particular be a monoclonal antibody, a chimeric antibody or a humanised antibody such as defined above.

In a preferred embodiment, when the immunoglobulin of the invention is a chimeric antibody such as defined above, the CH and CL regions associated with the VH and VL regions derive from a human immunoglobulin binding to the CD32 receptor, in particular a human immunoglobulin binding to the CD32B receptor or a human immunoglobulin of IgG$_1$ type.

In another preferred embodiment, the ligand of the CD32 receptor or the immunoglobulin of IgG$_1$ type according to the invention is a fragment of immunoglobulin, in particular a fragment of IgG$_1$ antibody. In particular, the fragment of immunoglobulin may be a Fab, F(ab')$_2$, Fab', ds(Fv)$_2$, sc(Fv)$_2$, Fc fragment or a "diabody". Further preferably, the fragment of immunoglobulin antibody is the Fc region of an immunoglobulin, in particular the Fc region of an IgG$_1$ antibody.

In another particularly preferred embodiment, the immunoglobulin binding to the CD32 receptor of the invention binds to the receptor via its Fc region.

In another particular embodiment, the ligand of the CD32 receptor according to the invention is a chimeric molecule comprising (i) the Fc region of an immunoglobulin binding to the CD32 receptor, preferably to the CD32B receptor and (ii) the Fab fragment of an immunoglobulin recognizing an allergen or an antigen.

In yet another embodiment, the ligand of the CD32 receptor of the invention is a chimeric molecule comprising (i) the Fc region of an immunoglobulin binding to the CD32 receptor, preferably to the CD32B receptor, and (ii) an allergen or an antigen.

The inventors have shown that surprisingly immunoglobulins of any idiotype, and not only anti-IgE antibodies, were capable of inducing an improvement in the symptoms of allergic asthma when administered via sublingual route.

Therefore, in a particular embodiment, the immunoglobulins of the invention may be immunoglobulins of any idiotype, and not necessarily anti-IgE antibodies. In another particular embodiment, the immunoglobulins of the invention may be specifically directed against a compound selected from the group consisting of an antigen, an allergen, an IgE and a cytokine. In yet another embodiment, the immunoglobulins of the invention may be specifically directed against a compound other than an IgE, or in other words, are not anti-IgE antibodies.

By "allergen" is meant herein any substance triggering an allergy. Non-limiting examples of allergens can be allergens of pollen (from trees, graminaceous plants, etc.), allergens of dust mites (from house or storage dust), insect allergens (from hymenoptera, cockroaches, etc.), animal allergens (from dog, cat, horse, rat, mouse etc.), mould allergens and food allergens. The allergen may for example be one of the allergens listed in the section "Therapeutic applications".

By "antigen" is meant any substance capable of triggering an immune response intended to remove it from the organism. It is generally a substance foreign to the organism. For autoimmune diseases the antigen may be a <<self>> antigen wrongly recognized as being a foreigner to the organism (auto-antigen).

By "cytokine" is meant here any protein other than an antibody secreted by a cell upon contact with a specific antigen and acting as cell mediator in the generation of an immune response. Non-limiting examples of cytokines can be interferons, such as IFN-α, IFN-β, IFN-ω and IFN-γ; interleukins such as IL-1, IL-2, IL-3, IL-4, IL-5, IL-6, IL-7, IL-8, IL-9, IL-10, IL-11, IL-12, IL-13, IL-17, IL-18 and IL-23; chemokines such as chemokines of the CXC family, chemokines of the CC family, chemokines of the CX3C family and chemokines of the C family; TNF, CSFs and TGFs.

In particular, the immunoglobulin of the invention may be an anti-IgE antibody, preferably non-idiotypic.

In addition the inventors have shown that surprisingly it was possible to induce an improvement in allergy symptoms by using immunoglobulins, in particular IgG$_1$s whether or not in sialylated form.

Therefore in a particularly preferred embodiment of the invention, the immunoglobulins of the invention are not in sialylated form.

By "sialylation" is meant herein the addition of a sialic acid residue on a protein which may in particular be a glycoprotein.

Within the context of the invention, the term "sialic acid" includes a family of sugars containing 9 or more carbon atoms, comprising a carboxyl group. A generic structure encompassing all the natural forms of sialic acid is shown in formula (I) below:

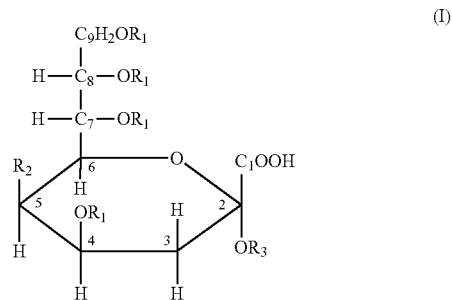

wherein:
the $R_1$ groups, at varied positions on a single molecule, can be the same or different from each other. $R_1$ can be a hydrogen or an acetyl, lactyl, methyl, sulfate, phosphate, anhydro, sialic acid, fucose, glucose or galactose group;

$R_2$ can be an N-acetyl, N-glycolyl, amino, hydroxyl, N-glycolyl-O-acetyl or N-glycolyl-O-methyl group;

$R_3$ represents the preceding sugar residue in an oligosaccharide to which sialic acid is attached in the context of a glycoprotein. $R_3$ can be a galactose (connected at position 3, 4, 5 or 6), an N-acetyl-galactosamine (connected at position 6), an N-acetyl-glucosamine (connected at position 4 or 6), a sialic acid (connected at position 8 or 9) or a 5-N-glycolylneuraminic acid.

More than 40 forms of sialic acid are found in nature, amongst which N-acetylneuraminic acid, N-glycolylneuraminic acid and their 0-acetylated derivatives, in particular N-acetyl-9-O-acetylneuraminic acid. The most common form of sialic acid is N-acetylneuraminic acid, in which $R_1$ is a hydrogen at all positions and $R_2$ is an N-acetyl group.

Within the context of the invention, by "immunoglobulin in sialylated form" is meant an immunoglobulin which contains at least one sialic acid such as defined above.

Within the context of the invention, by "immunoglobulin which is not in sialylated form" or "immunoglobulin in non-sialylated form" is meant an immunoglobulin which does not contain any sialylic acid such as defined above.

Anti-IgE Antibody Having the Capacity to Bind IgEs Fixed to their Receptors on the Surface of a Mastocyte and/or Basophile The invention also concerns an anti-IgE antibody, and in particular an anti-IgE antibody having the capacity of binding IgEs fixed to their receptors on the surface of a mastocyte or basophil without dissociating said IgEs from their receptors, intended to be used in the treatment of inflammatory diseases and manifestations, in particular of immediate allergy or type 1 hypersensitivity, an autoimmune disease, mastocytosis in particular mastocytosis induced by anaphylactic shock, or parasitosis.

By "IgE receptor" is meant the RFcεl receptor present on the surface of a mastocyte and/or basophil.

An anti-IgE antibody according to the invention may in particular be a monoclonal antibody, a chimeric antibody or a humanised antibody, such as defined above.

More particularly, the anti-IgE antibody of the invention may or may not be an anti-idiotypic antibody. Therefore the anti-IgE antibody of the invention can bind to any IgE, irrespective of the specificity of this IgE, or on the contrary the anti-IgE antibody is only able to bind to an IgE specifically directed against an antigen or a particular allergen.

In a preferred embodiment, when the anti-IgE antibody of the invention is a chimeric antibody such as defined above, the VH and VL regions associated with the CH and CL regions derive from an antibody directed against human IgEs.

In another preferred embodiment, when the anti-IgE antibody of the invention is a humanised antibody such as defined above, the donor antibody is a mouse, rat, rabbit, hamster antibody etc. and is specific to human IgEs. For example, CDRs of a mouse antibody specific to human IgEs can be grafted in the framework region of a human antibody to prepare a "humanised antibody" specific to human IgEs.

Preferably the anti-IgE antibody of the invention is a human or humanised antibody.

In another preferred embodiment, the anti-IgE antibody of the invention is a Fab, F(ab')$_2$, Fab', ds(Fv)$_2$, sc(Fc)$_2$ fragment or a "diabody".

The IgEs are capable of binding via their constant Fc parts to the RFcεl receptors present on the surface of mastocytes and basophiles. The anti-IgE antibody of the invention may have the capability of binding to IgEs fixed to the RFcεl receptors of a mastocyte or basophil without dissociating said IgEs from their receptors.

Prior research focused on the regions involved in the binding of IgEs with the RFcεl receptors. These regions have been identified as being the Cε3 domain and partly the Cε4 domain (Schwarzbaum et al. (1989) *Eur. J. Immunol.* 19: 1015-1023), or the Cε2, Cε3 domain and the region between the Cε2 and Cε3 domains (Takemoto et al. (1994) *Microbiol. Immunol.* 38: 63-71).

It is therefore preferable according to the invention that the anti-IgE antibody recognizes a part of the IgE not involved in the fixation of the IgE to its receptor on the mastocytes or basophiles. Preferably, the anti-IgE antibody of the invention is able to recognize the parts of the Cε2, Cε3 Cε4 domains not involved in the binding to the RFcεl receptor, the Cε1 domain, the variable regions of the heavy chain (VH) or light chain (VL) and the constant region of the light chain of the IgEs (CL).

In general, persons skilled in the art are capable of verifying the capability of a given antibody to fix to the IgEs bound to the RFcεl receptor using usual methods in the technical area. For example, the skilled person is able to verify that the adding of an anti-IgE antibody does not prevent the fixing of IgE to the RFcεl receptors on the surface of basophiles or mastocytes. According to its specificity, the anti-IgE antibody of the invention may optionally prevent the recognition of the allergen by the IgE, for example by creating steric hindrance at the recognition site of the antigen.

According to a preferred embodiment, the anti-IgE antibody has the capacity of bridging IgEs fixed onto their receptors on the surface of a mastocyte or a basophile.

The term "bridging of the IgEs" refers to the setting up of cross bonds between two IgEs each bound with a RFcεl receptor on the surface of a mastocyte or a basophil. These cross bonds are caused by the recognition of at least two IgEs, bounded to RFcεl receptors on the same cell by one same bridging molecule (allergen, anti-IgE antibody) and induce the activation of mastocytes or basophiles.

When a sufficient quantity of surface IgE is bridged i.e., when a sufficient quantity called an <<optimal quantity>> of bridging molecules is present, the cross bonds are able to induce the degranulation of mastocytes and basophiles and lead to the release of pro-inflammatory mediators.

This bridging capability of IgEs can be evaluated by persons skilled in the art, for example using a cell test allowing the detection of degranulation or activation of mastocytes or basophiles in the presence of an optimal quantity of anti-IgE antibodies. Degranulation can be estimated for example by measuring the quantity of histamine or β-hexosaminidase released during this degranulation by measuring for example by flow cytometry, the presence of CD63 and/or CD107a on the surface of mastocytes or basophiles.

Alternatively, it is also possible to measure the activation of cells further to bridging in the presence of anti-IgE antibodies by flow cytometry, by measuring the presence of CD203c on the surface of the mastocytes or basophiles. The anti-IgE antibody may in this case be tested at a <<suboptimal>> concentration which here refers to a concentration of anti-IgE antibody insufficient to induce degranulation of mastocytes or basophiles.

The anti-IgE antibodies of the invention may be antibodies belonging to any class of immunoglobulin, specific to an IgE and preferably capable of binding to IgEs fixed to the RFcεl receptors of a mastocyte or basophile without dissociating said IgEs from their receptors, and preferably capable of inducing the bridging of IgEs fixed to the RFcεl receptors of mastocytes and basophiles.

The anti-IgE antibody of the invention can in particular be an antibody having the capacity to bind to the CD32 receptor, in particular to the CD32B receptor such as defined above. Preferably the anti-IgE antibody of the invention is an antibody of IgG$_1$ type.

As examples of antibodies specific to murine IgEs, mention may be made of IgG1κ from the R35-72 clone (BD Biosciences Pharmingen, San Diego, Calif., USA), IgG1κ from the 23G3 clone (Southern Biotechnology Associates, Birmingham, Ala. Posner et al. (2004) *Biochemistry* 43: 11352-11360, Keegan et al. (1991) *Mol. Immunol.* 28: 1149-1154), IgG2a from the clones E11AC2IIC3, E11BA1ID1, E11BA3ID4, E9AD2IIA5, E11BB5IA6, E5BB3IIA4 and IgG1 from the E5AA1IA6 clone (Hook et al (1991) *Mol. Immunol.* 6: 631-639), IgG2a from the C12B9 clone (Keegan et al. (1991) *Mol. Immunol.* 28: 1149-1154), IgG2a from the LO-ME-2 clone (Kang et al. (2007) *Immune Network* 7: 141-148) or a fragment or a humanised form thereof As examples of bridging antibodies specific to human IgEs, mention may be made of the IgG1 from the E124.2.8 clone (Beckman Coulter).

The antibodies, in a preferred embodiment, may be chimeric or humanised antibodies derived from the above-cited antibodies.

The anti-IgE antibodies of the invention are preferably administered via mucosal route. More preferably, the anti-IgE antibodies of the invention are administered via sublingual route.

Methods of Producing Antibodies

The antibodies of the invention can be produced using any known technique such as for example chemical, biological, genetic, enzymatic techniques or combinations thereof.

The chimeric or humanised antibodies of the invention can be obtained using any means known to persons skilled in the art, in particular by genetic engineering of antibodies.

The construction of a chimeric antibody consists in isolating the DNA coding for the VH region and the VL region of a donor monoclonal antibody and in binding it with the DNA coding for the constant CH and CL regions of a human immunoglobulin.

A humanised antibody is obtained by replacing the hypervariable regions of a receiver monoclonal antibody by the hypervariable regions of a donor antibody ("CDR grafting") and may optionally need the following steps:

i) Designing the humanised antibody:
   determining CDR regions of the donor antibody to be transferred, and optionally identification of the residues of the framework regions of the donor antibody which are also to be transferred because of their roles in maintaining the structure of the CDRs, or their contributions to the antigen binding site. These regions or residues can be identified during the construction of a 3D model of the variable regions of the antibody and by the use of computer software such as RASMOL,
   identifying in databases of the most appropriate human antibody for humanisation and choice of the human isotype. For example, a suitable antibody for humanisation may be an antibody having framework regions close to those of the donor antibody.

ii) synthesis of the variable regions thus designed e.g. by PCR amplification of overlapping sequences and obtaining of the humanised antibodies.

Persons skilled in the art who know the amino acid composition of the desired sequence are capable of producing antibodies using standardized techniques for producing polypeptides. For example, they may be synthesized in solid phase, preferably using marketed peptide synthesis apparatus, such as the one produced by Applied Biosystems, California (USA), and following the manufacturer's instructions.

Alternatively, the antibodies of the invention can be produced using recombinant DNA techniques in an adapted expression system. The term "expression system" designates a cell host and a compatible vector under suitable conditions i.e. conditions allowing the expression of the protein encoded by the foreign DNA carried by the vector and introduced into the host cell. Typically, the nucleic acid sequences coding for an antibody can be inserted in a suitable expression vector which is then introduced into an adequate prokaryote or eukaryote host which will produce the desired antibody.

The terms "vector", "cloning vector" and "expression vector" relate to vehicles by means of which the DNA or RNA sequences coding for the antibody can be introduced into a host cell so as to transform the latter and allow the expression (i.e. the transcription and translation) of the introduced sequence. An expression vector is typically a plasmid, a cosmid, an episome, an artificial chromosome, a phage or a viral vector.

As viral vectors, mention may be made of adenoviruses, retroviruses, herpes virus and vectors derived from the adeno-associated virus (AAV). Such recombinant viruses can be produced using well known techniques such as the transfection of cell lines enabling their encapsidation or by transient transfection with plasmids or complementation viruses expressing the necessary missing functions. Mention may be made for example of the cell lines allowing encapsidation PA317, PsiCRIP, GPenv+, 293 etc. The detailed protocols enabling producing such defective recombinant viruses for replication are available in patent applications WO 95/14785, WO 96/22378, U.S. Pat. No. 5,882,877, U.S. Pat. No. 6,013,516, U.S. Pat. No. 4,861,719, U.S. Pat. No. 5,278,056 and WO 94/19478.

The host cells are transfected, infected or transformed by a nucleic acid or suitable vector such as described above. The term <<transformation>> relates to the introduction of a foreign gene (extrinsic or extracellular) of a DNA or RNA sequence in a host cell such that this host cell expresses the introduced gene, the DNA or RNA sequence for producing the desired substance typically the protein encoded by the gene or introduced sequence.

Usual expression systems include host cells and plasmid vectors of *E. coli*, insects host cells and vectors of Baculovirus type as well as mammalian cells and vectors.

One production method from a host cell expressing an antibody of the invention may comprise the steps consisting of: (i) in vitro or ex vivo introduction of a recombinant nucleic acid or vector such as described above into the competent host cell, (ii) in vitro culture of the recombinant host cell thus obtained, (iii) optionally selecting the cells which express and/or secrete said antibody or polypeptide.

Also, a method for producing the antibody of the invention may comprise the steps consisting of: (i) culture of the above-described transformed cell under suitable conditions for expression of the antibody; and (ii) collection of the antibody thus expressed.

The antibodies can be separated from the culture medium using conventional immunoglobulins purification methods such as purification on A-Sepharose protein, chromatography on hydroxylapatite, gel electrophoresis, dialysis or affinity chromatography.

The Fab fragment of the invention can be obtained by treating the antibodies with a protease, the papain. This Fab fragment can also be produced by insertion of a DNA encoding the Fab fragment of the antibody in a vector which can be used in a prokaryote or eukaryote expression system, and introduction of this vector into the suitable prokaryote or eukaryote for expression of the Fab fragment.

The F(ab')$_2$ fragment of the invention can be obtained by treating an antibody with a protease, the pepsin. The F(ab')$_2$ fragment can also be obtained by joining Fab' fragments such as described below together via a thioether link or disulfide bridge.

The Fab' fragment of the invention can be obtained by treating the F(ab')$_2$ complex of an antibody with a reducing agent, the dithiothreitol. The Fab' fragment can also be produced by inserting a DNA coding for the Fab' fragment of the antibody into a vector which can be used in a prokaryote or eukaryote expression system, and introducing this vector into the appropriate prokaryote or eukaryote to express the Fab' fragment.

The sc(Fv)$_2$ fragment of the invention can be produced by obtaining a cDNA sequence coding for the VH and VL regions previously described, followed by the insertion of this DNA into a vector which can be used in a eukaryote or prokaryote expression system, and introducing this vector into the appropriate eukaryote or prokaryote to express the sc(Fv)$_2$ fragment. To obtain a humanized sc(Fv)$_2$ fragment, it is possible to use the previously described technique of CDR grafting. This technique entails the selection of complementarity regions (CDRs) of a donor sc(Fv)$_2$ fragment and grafting thereof onto the framework of a human sc(Fv)$_2$ fragment of known three-dimensional structure (see for example WO 98/45322; WO 87/02671; U.S. Pat. Nos. 5,859,205; 5,585,089; 4,816,567; EP0173494).

Therapeutic Compositions

The present invention also concerns pharmaceutical compositions, preferably for administration via mucosal route, more preferably for administration via sublingual route, comprising an immunoglobulin of $IgG_1$ type such as defined above and/or a ligand of the CD32 receptor such as defined above and/or an anti-IgE antibody such as defined above.

In a particular embodiment, the pharmaceutical composition of the invention may further comprise an allergen such as defined above or an antigen.

The antibodies and ligands of the invention may be combined with pharmaceutically acceptable excipients and optionally with sustained-release matrixes such as biocompatible polymers for example to form therapeutic compositions. Said polymers for example may be polysaccharides such as starch, pectins, amylopectins, chitosan or particles or polysaccharide particles (CPS) such as described by Razafindratsita et al. (2007, *J. Allergy Clin Immunol*. 120: 278-285) and possibly being in the form of nano-particles or microparticles.

For combined therapies, the pharmaceutical compositions may comprise both the antibodies of the invention and a specific desensitization treatment and/or symptomatic treatment of the allergy. As examples of specific desensitization treatment mention may be made of any treatment comprising the administration of allergenic extracts. Symptomatic treatments may comprise anti-inflammatory substances (such as corticosteroids or anti-histaminics), leukotriene inhibitors, broncho-dilatators, sodium cromoglycate, theophylline.

The term "pharmaceutically acceptable" relates to molecules and compositions which do not induce any allergic adverse or undesirable reactions when they are administered to mammals and in particular to humans. A pharmaceutically acceptable vehicle or excipient may be a solid or a semi-solid, a liquid, a diluent, an encapsulated material or any other formulation.

The form of the pharmaceutical composition, the mode of administration, the dose and dosage may evidently depend inter alia on the disease to be treated, on its symptoms and the severity thereof, the patient's age, weight and gender.

The pharmaceutical or therapeutic composition of the invention may be formulated so that it can be administered via mucosal, sublingual, oral, nasal, vaginal, rectal, bronchial, auricular, transdermal, sub-cutaneous/intra-dermal, conjunctival, topical, parenteral, intraveinous, intramuscular or intraocular route. Preferably, the pharmaceutical or therapeutic composition is administered via sublingual, oral, nasal, vaginal, rectal, bronchial, auricular, transdermal, sub-cutaneous/intra-dermal or conjunctival route. More preferably, the pharmaceutical or therapeutic composition is administered via mucosal route and in particular via buccal, sublingual, nasal, oral, bronchial, rectal, vaginal or auricular route. Most preferably the pharmaceutical or therapeutic composition is administered via sublingual route.

The pharmaceutical compositions of the invention may optionally contain suitable, pharmaceutically acceptable excipients so that they can be injected (in particular these may be isotonic and sterile saline solutions, monosodium or disodium phosphate, sodium, potassium, calcium or magnesium chloride, etc, or a mixture of these salts). These compositions may also be dry compositions, in particular dry and frozen, freeze-dried or refrigerated compositions which, after the addition of sterile water or physiological water accordingly, form solutions for injection.

The doses used may be adapted in relation to different parameters such as in particular the administration mode, the type of pathology or alternatively the envisaged treatment time. Preferably the dose is adapted to allow a single treatment using a single dose.

To prepare the pharmaceutical compositions, a sufficient quantity of antibody can be dissolved or dispersed in a pharmaceutically acceptable vehicle or aqueous medium.

The pharmaceutical forms suitable for use via injection comprise solutions of sterile water, dispersions, formulations with sesame oil or aqueous propylene glycol, and sterile powders for extemporaneous preparation of sterile injectable solutions. In all cases, the form used must be sterile and must be sufficiently fluid so that it can easily be injected using a syringe. It must be stable under production and storage conditions and must be protected against contaminations by microorganisms, such as bacteria or fungi.

The solutions of active compounds whether in free form or as acceptable salts from a pharmaceutical viewpoint may be prepared with water mixed with a surfactant such as hydroxypropylcellulose. The dispersions can be made in glycerol, in liquid polyethylene glycols, in a mixture of both or in oils. These preparations generally contain a preserving agent to prevent the growth of micro-organisms under normal conditions of storage and use.

After formulation in the form of a medicament, the solutions can be administered in a manner compatible with the dosage of the formulation and in a therapeutically active quantity. The medicaments can be administered as described above, but also in the form of release capsules.

The administration via sublingual route is particularly preferred. When administered via sublingual route, the pharmaceutical composition reaches the cells of the mucosa and optionally the cells of the sub-mucosa. This mode of administration has the advantage of being simple, rapid and avoids passing through the gastro-intestinal tract where the pharmaceutical composition risks degradation by digestive enzymes. A pharmaceutical composition for administration via sublingual route may preferably be formulated in the form of drops (possibly containing glycerol) or tablets.

Preferably, when the antibodies and/or pharmaceutical compositions of the invention are administered via mucosal route, in particular via sublingual route, they are not directly accessible to the DC-SIGN receptors. By "DC-SIGN" ("Dendritic Cell-Specific Intercellular adhesion molecule-3-Grabbing Non-integrin"), or "CD209", is meant herein a type C lectin having strong affinity for sialic acid.

For parenteral administration in the form of an aqueous solution, for example, the solution may optionally be buffered in a suitable manner and the diluent can first be made isotonic through the addition of a sufficient quantity of salt or glucose. These aqueous solutions are particularly preferred for administration via intravenous, intra-muscular, subcutaneous and intraperitoneal route. In the light of this disclosure, persons skilled in the art will know which type of aqueous solution can be used. For example, a dose can be diluted in 1 ml of isotonic NaCl solution or it can be added to 1000 ml of "hypodermoclysis" fluid or injected directly at the planned injection site (see for example "*Remington's Pharmaceutical Sciences*" 15th Edition, 1035-1038 and 1570-1580). Some variations in the dosage may be necessary according the condition of the subject to be treated. The person in charge of administering the medicament can determine the suitable dose for each individual.

The ligands of the CD32 receptor or immunoglobulins according to the invention may be added to a therapeutic mixture in a quantity of about 0.001 to 1000 milligrams or about 0.01 to 500 milligrams or about 1 to 200 milligrams, or about 10 to 100 milligrams per dose, preferably of the order of 100 milligrams. Multiple doses can also be administered.

Preferably the ligand of the CD32 receptor or the immunoglobulin of the invention is administered at suboptimal concentration i.e. a concentration insufficient to induce degranulation of mastocytes or basophiles. The suboptimal concentration of an antibody according to the invention can be determined easily by those skilled in the art. For example they may test the effect of different concentrations of antibodies on mastocytes and basophiles. The suboptimal concentration will correspond to any concentration lower than the minimum concentration (optimal concentration) inducing degranulation. Preferably the suboptimal concentration is determined during clinical trials in human or animal.

In addition to the compounds formulated for parenteral administration, such as intravenous or intramuscular injections, other pharmaceutical forms are acceptable including for example tablets or other solid administration forms, delayed release capsules or any other usable form.

In some embodiments of the invention, the use of liposomes and/or microparticles and/or nanoparticles can be envisaged to introduce antibodies into the host. The use and formation of liposomes and/or microparticles and/or nanoparticles are known to a skilled person.

Therapeutic Applications

Preferably the immunoglobulins and ligands of the invention are used to treat inflammatory diseases and manifestations.

By "inflammatory disease" is meant herein a disease associated with an inflammation. Examples of inflammatory diseases are well known to those skilled in the art and particularly include atherosclerosis, myocardial ischemia, acne, asthma, autoimmune diseases, prostatitis, glomerulonephritis, hypersensitivities, chronic intestinal inflammatory diseases, pelvic inflammatory diseases, rheumatoid polyarthritis, graft rejection, vasculitis, interstitial cystitis, allergies and inflammatory myopathies.

By <<inflammatory manifestations>> is meant herein inflammatory reactions which occur in the course of a disease which itself is not strictly inflammatory such as parasitosis or mastocytosis.

By "auto-immune disease" is meant herein a disease due to hyperactivity of the immune system against substances or tissues which are normally present in the organism. Examples of autoimmune diseases are well known to those skilled in the art and particularly include Berger's disease, Basedow's disease, Hashimoto's thyroiditis, primary myxoedema, coliac disease, haemorrhagic rectocolitis, Crohn's disease, primitive biliary cirrhosis, primitive sclerosing cholangitis, Biermer's anaemia, erythematous lupus, CREST syndrome, type 1 insulin-dependent diabetes, systemic sclerodermia, pemphigus vulgaris, bullous pemphigoïd, acquired bullous epidermolysis, herpetiform dermatitis, myasthenia, Lambert-Eaton's myasthenic syndrome, polymyositis, Goujerot-Sjögren syndrome, Guillain-Barré syndrome, disseminated erythematous lupus, multiple sclerosis, optical neuritis, psoriasis, rheumatoid arthritis, medullar aplasia, Reiter's syndrome, primitive biliary cirrhosis, antiphospholipid antibody syndrome, Opsoclonus Myoclonus syndrome, temporal arteritis, acute disseminated encephalomyelitis, Goodpasture syndrome, Wegener's granulomatosis, Churg-Strauss syndrome, sarcoidosis, nephrotic syndrome and La Peyronie disease.

Preferably the immunoglobulins and ligands of the invention and the compounds or medicaments comprising the immunoglobulin or ligand of the invention are used to treat immediate allergies, mastocytoses and parasitoses.

The term "immediate allergy" or "type 1 hypersensitivity" such as used herein means a humoral response in response to an allergen which differs from a normal humoral response by the fact that the plasmocytes secrete IgEs.

Among the clinical signs due to immediate allergies which can be treated with the antibody of the invention, as examples mention may be made of systemic anaphylaxis, localized anaphylaxis (atopia), allergic rhinitis, asthma, food allergies, atopical dermatitis, conjunctivitis, eczema, mastocytosis induced by anaphylactic shock, allergic signs caused by IgEs secreted in response to infection by a parasite. Particularly preferably, o, the context of the invention, the sign of immediate allergy is asthma.

In the invention, the allergy can be caused by exposure of an individual to any allergen.

Non-limiting examples of allergens may be pollen allergens (of trees, graminaceous plants, etc.), dust mite allergens (of house or storage dust), insect allergens (of hymenoptera, cockroaches, etc.), animal allergens (of dog, cat, horse, rat, mouse, etc.,), mould allergens and food allergens.

For example the allergen may be selected from the group consisting of allergen proteins of genus *Dermatophagoides*, the allergen proteins of genus *Felis*, the allergen proteins of genus *Ambrosia*, the allergen proteins of genus *Lolium*, the allergen proteins of genus *Cryptomeria*, the allergen proteins of genus *Alternaria*, the allergen proteins of genus Alder, the allergen proteins of genus *Betula*, the allergen proteins of genus *Blomia*, the allergen proteins of genus *Quercus*, the allergen proteins of genus *Olea*, the allergen proteins of genus *Artemisia*, the allergen proteins of genus *Plantago*, the allergen proteins of genus *Parietaria*, the allergen proteins of genus *Canis*, the allergen proteins of genus *Blattella*, the allergen proteins of genus *Apis*, the allergen proteins of genus *Cupressus*, the allergen proteins of genus *Thuya*, the allergen proteins of genus *Chamaecyparis*, the allergen proteins of genus *Periplaneta*, the allergen proteins of genus *Agropyron*, the allergen proteins of genus *Secale*, the allergen proteins of genus *Triticum*, the allergen proteins of genus *Cynorhodon*, the allergen proteins of genus *Juniperus*, the allergen proteins of genus *Dactylis*, the allergen proteins of genus *Festuca*, the allergen proteins of genus Poa, the allergen proteins of genus *Avena*, the allergen proteins of genus *Holcus*, the allergen proteins of genus *Anthoxanthum*, the allergen proteins of genus *Arrhenatherum*, the allergen proteins of genus *Agrostis*, the allergen proteins of genus *Phleum*, the allergen proteins of genus *Phalaris*, the allergen proteins of genus *Paspalum*, the allergen proteins of genus Sorghum. Examples of known allergen proteins derived from proteins of the genii listed above include: *Cynorhodon* Cyn d 1; *Dermatophagoides* (*pteronyssinus* or *farinae*) Der p 1; Der p 2; Der p 3; Der p 5; Der p 7; Der f 1; Der f 2; Der f 3; Der f 5; Der f 7; *Felis* (*domesticus*) Fel d 1; *Ambrosia* (*artemisiifolia*) Amb a 1; Amb a 2; Amb a 3; Amb a 4; *Lolium* (*perenne*) Lol p 1; Lol p 2; Lol p 3; Lol p 4; Lol p 5; Lol p 9; *Cryptomeria* (*japonica*) Cry j 1; Cry j 2; *Juniperus* (*sabinoides ou virginiana*) Jun s 1; Jun v 1; *Juniperus* (*ashei*) Jun a 1; Jun a 2; *Dactylis* (*glomerata*) Dac g 1; Dac g 5; Poa (*pratensis*) Poa p 1; Poa p 5; *Phleum* (*pratense*) Phl p 1; Phl p 5; *Anthoxanthum* (*odoratum*) Ant o 1; Ant o 5; *Betula* (*verrucosa*) Bet v 1; Bet v 2; Bet v 4 and Sorghum (*halepensis*) Sor h 1.

Food allergens may derive from milk, eggs, vegetables (including peanut and soybean), nuts and hazelnuts, wheat, crustaceans, fish and shellfish and derivative products thereof. In particular, food allergens may be ovalbumin or gluten.

Mastocytoses are orphan diseases in which the mastocytes proliferate abnormally. A distinction is made between two main types of mastocytosis: skin mastocytosis and systemic mastocytosis. Some cases of skin mastocytosis subsequent to hymenoptera bites have been associated with serious IgE-dependent anaphylactic accidents (Kraemer et al. (2004) *Rev. Fr. Allergol. Immunol. Clin.* 44: 414-416). The term <<mastocytosis>> according to the invention particularly designates mastocytosis induced by anaphylactic shock. The clinical signs due to mastocytoses which can be treated by the invention correspond to clinical signs due to IgE-induced mastocyte degranulation.

Parasitoses are diseases due to an infection by parasites. This infection often induces a Th2 response with IgE secretion. In some cases, this IgE response may induce clinical symptoms although it generally appears rather more to protect the body against signs of the parasite infection (Flohr et al. (2008) *Clin. Exp. Allergy* 39: 20-32). Examples of parasites can be helminths, cestodes, trematodes and nematodes. The clinical signs due to parasitoses which can be treated by the invention correspond to clinical signs due to IgE secretion, in particular allergic signs induced by IgEs secreted in response to an infection by a parasite.

Within the context of the invention, the term "treat" or "treatment" means to eliminate, alleviate or prevent the progression of a disorder or to prevent the onset of a said disorder or of one or more symptoms related to this disorder. In particular, the treatment of immediate allergies may consist of reducing or even preferably eliminating excessive inflammation due to the release by mastocytes and basophiles of pro-inflammatory molecules, through the administration of a therapeutically active quantity of antibodies according to the invention.

The term "patient" or "individual" according to the invention is used to designate a human or a non-human mammal (e.g. a rodent (mouse rat), a feline, a canid or a primate) which develops or risks developing an immediate allergy. Preferably the individual is a human. It may be a patient suffering from a mastocytosis or parasitosis.

The term "therapeutically active quantity" means a sufficient quantity of antibody to treat an immediate allergy, a mastocytosis or a parasitosis and having an acceptable benefit/risk ratio for medication treatment. The quantity of antibody and compositions according to the invention and the frequency of administration will be determined by clinical trials, by the physician or by the pharmacist. The "therapeutically active" dose specific to each of the patients could depend on a certain number of factors such as the type and severity of the disorder to be treated, the activity of the antibody used, the composition used, the patient's age, weight, general state of health, gender and regimen, the mode of administration, the time of treatment (single or multiple dose), the medicaments used in combination and other factors well known to medical specialists.

The invention is also described in the following figures and examples which are non-limiting.

FIGURES

FIG. 1 shows the effect on bronchial hyper-reactivity (measured in PenH value or <<enhanced pause>>), of stimulation with metacholine on a group of three BALB/c mice non-sensitized to ovalbumin (group 1) and groups of five mice after sensitization to ovalbumin and desensitization with:

group 2: PBS;
group 3: ovalbumin at a dose of 500 µg via sublingual administration, twice a week for two months;
group 4: the rat control isotype of IgG1κ type at a dose of 25 µg via sublingual administration, twice a week for two months;
group 5: rat anti-mouse IgE antibody of clone R35-72 at a dose of 25 µg via sublingual administration twice a week for two months;
group 6: rat anti-mouse IgE antibody of clone R35-72, at a dose of 10 µg via sublingual administration twice a week for two months.

Figure 2:
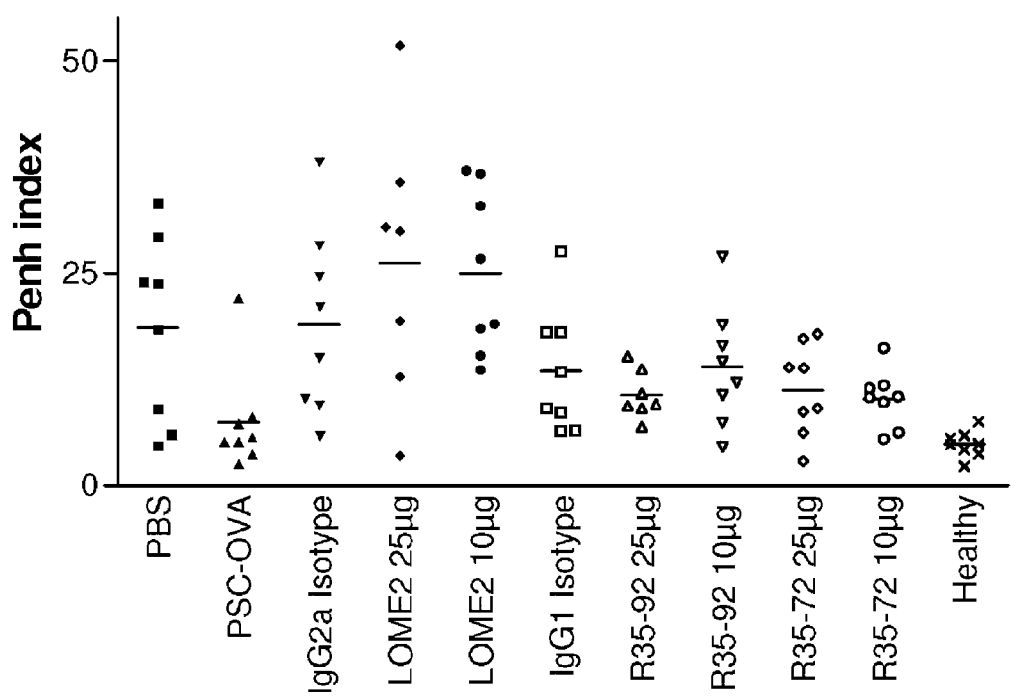

FIG. 2 shows the reactivity of the airways by measuring the Penh value in response to administration of metacholine (100 mg/ml). Eight mice were analyzed in each group. The horizontal bars represent the mean response in each group, each dot representing the Penh value obtained for a given animal. The results represent two independent experiments.

Figure 3:
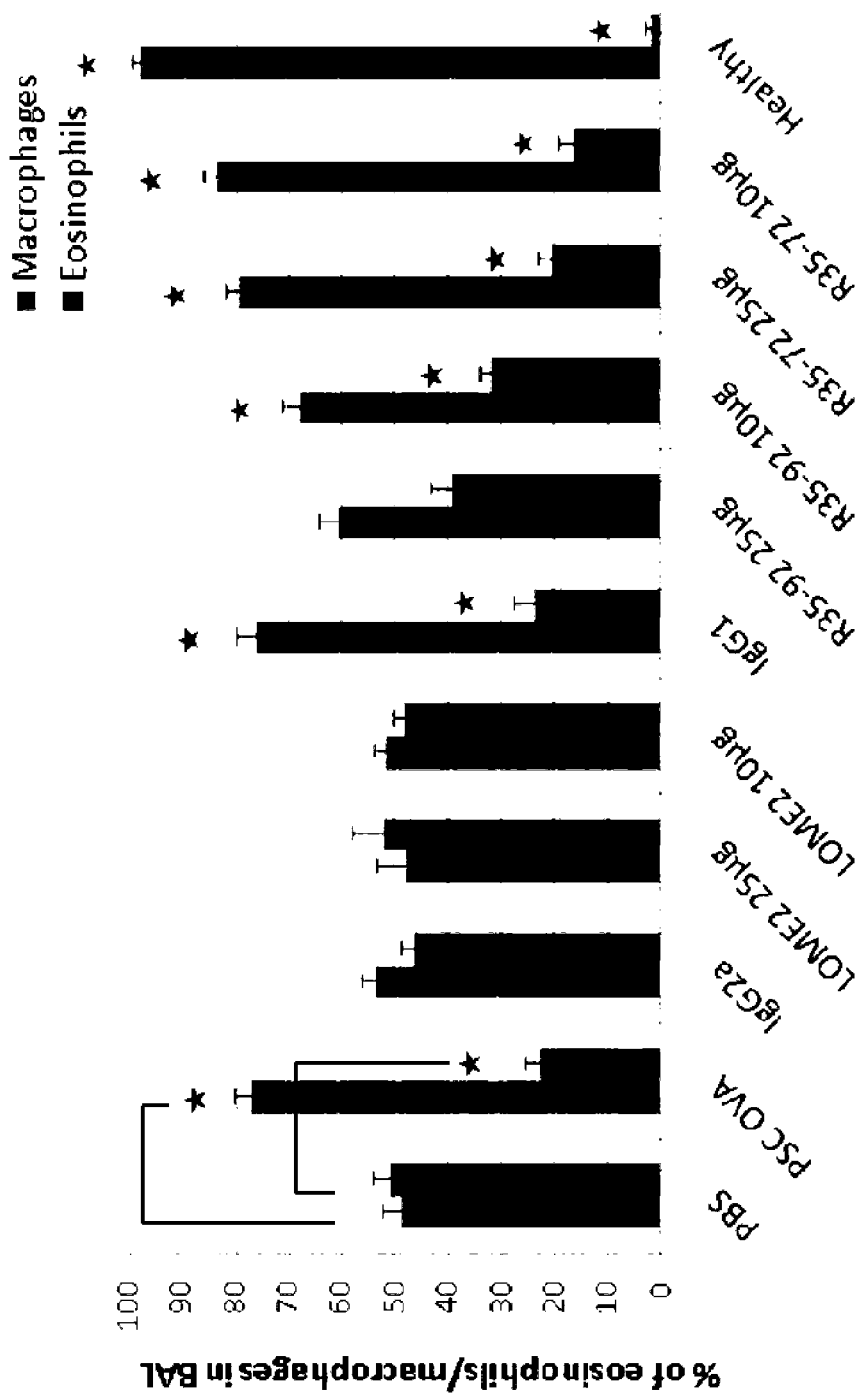

FIG. 3 shows the count of macrophages and eosinophils in bronchial alveolar washings of mice given various treatments. The results are given as the mean±standard deviation of the mean N=8 mice per group. * $p<0.05$ compared with mice desensitized with PBS (placebo). The data were compared using the non-parametric test (Kruskal-Wallis).

EXAMPLE 1

Material and Methods
Sensitization and Desensitization of Mice
BALB/c mice were sensitized with ovalbumin (OVA) as described in Razafindratsita et al. (2007, *J. Allergy Clin. Immunol.* 120: 278-285).

Groups of 5 mice were then treated via sublingual route twice a week for two months with:
500 µg OVA per administration;
10 or 25 µg of rat anti-mouse IgE IgG1 κ (clone R35-72, BD Biosciences Pharmingen, San Diego, Calif., USA) per administration;
25 µg of non-specific rat IgG1κ (control isotype; eBioscience, San Diego, Calif., USA) per administration or PBS for the group of control mice.

The mice were then subjected to allergenic challenge with aerosols of OVA (1% weight/volume), twice within two consecutive days.

In parallel, a group of three healthy mice not subjected to ovalbumin was used as control group.

The anti-IgE used, obtained from the R35-72 clone, was a rat antibody of IgG1κ type which is known for its ability to bind with IgEs on the surface of mastocytes and/or basophiles and of thereby inducing the release by these cells of pro-inflammatory mediators (Kubo et al. (2003) *J. Immunol.* 170: 775-780, Zhou et al. (2007) *J. Exp. Med.* 204: 2797-2802).

The non-specific rat IgG1κ monoclonal antibody has no specificity for murine IgEs.

Determination of Bronchial Hyper-Reactivity
The measurement of bronchial hyper-reactivity was performed 24 hours after the last challenge, by whole body plethysmography (Buxco Europe Ltd, Winchester, UK) as described by Hamelmann et al. (1997, *Am. J. Respir. Crit. Care Med.* 156: 766-775) and bronchial resistance was estimated by measuring PenH (enhanced pause). The PenH index was obtained by determining the ratio between the PenH values measured after exposure to inhalation of USA metacholine and after exposure to atomized PBS.

Results

To determine the effect on allergenic response of an anti-IgE antibody having the capacity to bind and bridge murine IgEs on the surface of mastocytes and basophiles, mice were sensitized with ovalbumin and then desensitized with this anti-IgE antibody. These mice were compared with mice sensitized to ovalbumin and then desensitized with the same ovalbumin, or desensitized with a control isotype, or non-desensitized. All these mice were compared with mice non-sensitized with ovalbumin.

Bronchial hyper-reactivity with metacholine was increased in mice sensitized to ovalbumin and treated with PBS (FIG. 1, group 2), as shown by the high value of the "PenH" parameter compared with the value obtained for mice non-sensitized with ovalbumin (FIG. 1, group 1).

An improvement in bronchial hyper-reactivity was observed in mice sensitized then desensitized with ovalbumin (FIG. 1, group 3).

A greater improvement in bronchial hyper-reactivity was observed in mice sensitized with ovalbumin then desensitized in increasing order of improvement, with:
    anti-IgE at a dose of 10 µg per administration (FIG. 1, group 6);
    the control isotype at a dose of 25 µg per administration (FIG. 1, group 4);
    anti-IgE at a dose of 25 µg per administration (FIG. 1, group 5).

This example shows in most surprising manner that the administration of an anti-IgE antibody having the capacity to bind with IgEs on the surface of mastocytes and basophiles without dissociating said IgEs from their receptors, allows a very substantial reduction to be induced in the bronchial hyper-reactivity of mice sensitized to ovalbumin.

This decrease is dependent upon the quantity of administered anti-IgE and is much more efficient than desensitization with ovalbumin and at molar concentrations at least 60 times less (bearing in mind that the molecular weights of ovalbumin and of an immunoglobulin are respectively 45 kDa (Nisbet et al. (1981) Eur. J. Biochem. 115: 335-345) and about 150 kDa.

At least part of the effect is related to the specificity of the anti-IgE, as indicated by the difference in PenH value observed with 25 µg per administration between the anti-IgE and the control isotype, which is of the same order as the difference observed between the allergen (ovalbumin) and the placebo (PBS). The effect obtained with the control isotype may possibly be explained by the inducing of non-specific signals reducing the anaphylactic reaction at the time of fixation of this antibody onto the receptor with IgG inhibitor: RFcγIIb (Kang et al. (2007) Immune Network 7: 141-148).

EXAMPLE 2

This study shows the effect of bridging or non-bridging anti-IgE antibodies and of IgG, type antibodies administered via sublingual route in immunotherapy using an in vivo murine model of allergic asthma.

Material and Methods

Mice, Reagents and Antibodies

Female mice aged 6 to 8 weeks were obtained from Charles River (L'Arbresle, France). The phosphate buffer (PBS) was obtained from Invitrogen (Carlsbad, Calif.). Level V ovalbumin (OVA) with low endotoxin content was obtained from Sigma (St. Louis, Mo.) and was also purified on an endotoxin-removing gel (Pierce, Rockford, Ill.). The concentrations of residual endotoxin determined by the Endochrome K test (R1708K, Charles River, Wilmington, Mass.), were always less than 0.1 enzymatic unit (EU)/µg of protein. A polymerized form of corn maltodextrin (capsular polysaccharide or CPS) was used as system for administering a muco-adhesive particle antigen (Baudner et al. (2002) Infect. Immun. 70:4785-4790; Razafindratsita et al. (2007) J. Allergy Clin. Immunol. 120:278-285).

The monoclonal antibodies (mAb) cited in Table 1 were used as purified antibodies for sublingual administration.

TABLE 1

List of antibodies used.

| Antibody | Antigen | Species/Isotype | Manufacturer |
|---|---|---|---|
| LO-ME-2 | IgE (bridging) | Rat $IgG_{2a}/\kappa$ | Invitrogen, ref: 04-7000 |
| Control isotype | | Rat $IgG_{2a}$ | e-biosciences, ref: 14-4321 |
| R35-92 | IgE (non-bridging) | Rat $IgG_1/\kappa$ | BD Biosciences, ref: 553416 |
| R35-72 | IgE (bridging) | Rat $IgG_1/\kappa$ | BD Biosciences, ref: 553413 |
| Control isotype | | Rat $IgG_1/\kappa$ | e-biosciences, ref: 14-4301 |

Purification of Antibodies

To obtain all the antibodies in an identical buffer, the samples of anti-IgE were dialysed against 10 volumes of PBS using 30 kD membranes (Amicon Ultra-4, Millipore Corp.). The desalted samples were also filtered (Millex 0.22 µm, Millipore Corp.) to prevent any bacterial growth in the absence of sodium azide. Finally, the protein concentrations were determined using optical density of 280 nm (OD280) (Secoman XL, Uvikon) before and after filtration.

Sublingual Immunotherapy in BALB/c Mice

For sensitization, the mice were immunized via intraperitoneal route (i.p.) at days 0 and 14 with 10 µg OVA adsorbed on 2 mg $Al(OH)_3$, administered in 100 µl PBS. On day 21, a challenge test of 20 min using an aerosol was performed with 1% (weight/volume) OVA over 4 consecutive days using an aerosol administration system (Buxco Europe Ltd, Winchester, UK). To induce tolerance, the anti-IgE antibodies (10 µg and 25 µg per dose) were applied via sublingual route to groups of 8 mice, twice a week for 2 months. The control mice were treated via sublingual route with PBS or isotypic antibodies ($IgG_1/\kappa$ and $IgG_{2a}$). As positive efficacy controls, some mice were treated via sublingual route with CPS-OVA (500 µg). Airway hyper-reactivity measurements (AHR) were performed by whole body plethysmography (Puxco Europe Ltd, Winchester, UK) and the results were expressed by lengthening the pause ("enhanced pause" or Penh). The Penh index, expressed as an increase relative to the basal resistance of the airways, was obtained by dividing the Penh value measured after exposure by inhalation to increasing doses of metacholine (0 to 100 mg), by the Penh value measured after inhalation of atomized PBS, as described in Razafindratsita et al. (2007).

For the analysis of inflammatory cells in bronchial-alveolar washings (BAL), the mice were anaesthetized by intraperitoneal injection of pentobarbital (50 mg/kg body weight), and BALs were performed with 3×400 µl PBS. The BAL fluid was centrifuged at 800 g for 10 min at 4° C. The cell pellets were re-suspended in PBS and left to rotate on glass slides by cytocentrifugation, fixed and labelled with May/Grunwald Giema (RAL Reagents, Martillac, France).

The eosinophils and macrophages were counted under optical microscopy using 200 times magnification.

Antibody Response

Samples of blood were collected at the retro-orbital sinus to evaluate the levels of antibodies specific to OVA using ELISA. The sera were collected after centrifugation at 10000 rpm for 10 min. For the detection of the $IgG_1$ and $IgG_{2a}$ antibodies, purified OVA (0.2 µg) was plated overnight at 4° C. on ELISA plates (Nunc, Roskilde, Denmark). After the steps of washing and saturation, the mouse sera dilutions (1/100 to 1/12800 for $IgG_1$ and 120 to 1/12560 for $IgG_{2a}$) were incubated for 1 h at 37° C. The plates were washed and anti-mouse biotinylated rat $IgG_1$ (dilution 1/100, BD Pharmingen, San Jose, Calif.) or $IgG_{2a}$ antibodies (dilution 1/200, BD Pharmingen) were added for 1 h at 37° C. Anti-mouse rat IgG antibodies conjugated with streptavidine-peroxidase (dilution 1/400, BD Pharmingen) were used for detection, using orthophenylenediamine (OPD) as substrate (Sigma Chemicals Aldrich). The reaction was stopped with 3N HCl and the optical densities were determined using an ELISA plate reader at 492 nm (Labsystems, Helsinki, Finland).

For the detection of IgE antibody titres, anti-mouse IgE antibodies (1 µg/well, Bethyl Laboratories, Montgomery, Tex.) were plated on ELISA plates. After the steps of washing and saturation, dilutions of mouse sera (1/10 to 1/320) were incubated for 1 h at 37° C. Digoxygenin-OVA was incubated (at 1/10 dilution) for 1 h at 37° C. and Fab fragments of mouse anti-digoxygenin antibodies conjugated with horseradish peroxidase (HRP) (Roche) were used for detection at a dilution of 1/1000. A 2,2'-azino-bis(3-ethyl-benzthiazoline-6 sulfonic) acid substrate (ABTS) was added (Roche). The optical densities were measured using an ELISA plate reader at 405 nm.

The antibody titres were defined as the reverse of the last dilution at which the value of the optical density was twice higher the background noise.

To determine the levels of antibodies specific to the allergen at the mucosal surfaces, samples of saliva were collected for determining the IgA level by ELISA. In brief, microplates were coated with goat anti-mouse IgA (0.1 µg/well, Bethyl Laboratories), washed and dilutions of the supernatant (1/20 to 1/320) were incubated for 1 h at 37° C., followed by digoxygenin-OVA (dilution 1/100). The plates were washed and rabbit anti-digoxygenin antibodies conjugated with HRP (Roche) were used for detection as described above.

Statistical Analysis

The data were compared using a non-parametric test (Kruskal-Wallis). The results were considered to have statistical significance at a p value of less than 0.05.

Results

The Anti-IgEs of Clones R35-72 and R35-92 and the Corresponding $IgG_1$/κ Isotypes Improve Clinical Efficacy in Mice Specifically Sensitized with OVA and in Pulmonary Inflammation.

As described above, the mice sensitized with OVA develop airway hyper-reactivity (AHR) associated with high Penh values detectable by whole body plethysmography, and signs of lung inflammation with cell infiltrations. Anti-IgE antibodies (clones LO-ME-2, R35-72 and R35-92) were tested as candidates for immunotherapy in this in vivo murine model of established asthma. Antibodies of the corresponding isotype and CSP-OVA were used as controls in these experiments.

As shown in FIG. 2, and as expected, the healthy mice (i.e. non-sensitized) displayed low Penh values whilst the mice sensitized with OVA and treated via sublingual route with PBS (placebo) displayed strong AHR. The mice sensitized with OVA and treated via sublingual route with CSP-OVA were used as positive control and exhibited low Penh values. Sublingual treatment with the $IgG_{2a}$/κ isotype control or with anti-IgE antibodies (isotype $IgG_{2a}$/κ) of the LO-ME-2 clone (10 or 25 µg) did not have any impact on AHR. On the contrary, sublingual treatment with anti-IgEs (isotype $IgG_1$) of the clones R35-72 and R35-92 induced a reduction in AHR in most of the animals compared with the mice treated with PBS. Surprisingly, the $IgG_1$ isotype control induced a similar reduction in AHR suggesting that immune mechanisms non-specific of the antigen are involved in the induction of tolerance in this model.

The reduction in AHR observed after treatment with the anti-IgEs corresponding to the clones R35-72 and R35-92 (10 or 25 µg) and the corresponding isotype control $IgG_1$ was associated with a significant decrease ($p<0.05$) in the number of eosinophils in the BALs as observed with the positive control CSP-OVA (FIG. 3).

The Therapeutic Sublingual Administration of Anti-IgE Antibodies does not Alter the IgG, IgE or IgA Responses.

Sublingual immunotherapy (SLIT) with anti-IgE antibodies of the LO-ME-2 clone (isotype $IgG_{2a}$/κ) increased the $IgG_1$ and IgE specific to OVA only at the dose of 10 µg. In all the other experimental groups there was no detectable change in the IgE or IgG sera antibodies specific to OVA. The levels of OVA-specific salivary IgA antibodies were increased in mice treated with CSP-OVA compared with mice which had been given PBS. On the other hand, none of anti-IgE antibodies or control antibodies with the corresponding isotypes altered the level of IgA antibodies specific to OVA.

This study therefore shows that anti-IgE antibodies of isotype $IgG_1$/κ of the R35-72 and R35-92 clones allow an increase in tolerance induction. In addition, the control isotype antibodies $IgG_1$/κ also promote the induction of tolerance. On the contrary, anti-IgE antibodies of isotype $IgG_{2a}$/κ of the LO-ME-2 clone and the $IgG_{2a}$/κ isotype control antibodies do not alter lung function in mice sensitized to OVA. Therefore, these data suggest that the tolerance-inducing effect of the anti-IgE antibodies of the R35-72 or R35-92 clones could involve the Fc region of the $IgG_1$/κ isotypes. This raises the possibility that said anti-IgE antibodies could mediate their tolerance-inducing effect both by binding with the IgEs linked to FcεRI via their Fab regions, and by binding with the regulator receptor FcγRIIb, via their Fc region.

EXAMPLE 3

This study shows the distribution of the Fc receptors of IgGs in the tongue tissues of mice, and the characterization of N-glycosylation of the Fc regions of the antibodies used in Example 2.

Material and Methods

Immuno-Histology

For immunohistology, tissues taken from the spleen and tongue were sampled from naive mice frozen at −80° C. Tissue sections (4-6 µm in width) were cut in series, air-dried for at least 30 min, fixed in acetone for 1-2 min, and incubated for 10 min in 3% hydrogen peroxide (Sigma) to block endogenous peroxidase activity. After washing in Tris buffer (TBS: 0.05 M Tris, 0.15 M NaCl, pH 7.4), the primary antibodies i.e. anti-CD16/32 (clone 2.4G2, BD Biosciences) or anti-SIGN-R1 (clone ER-TRP9, Abcam) (dilution 1/100 in TBS) were added to the samples and incubated for 1 h at room temperature. The tissue sections were washed in TBS and incubated with biotinylated rabbit anti-goat secondary IgG antibodies (Sigma, 1/400) for 30 min before adding biotin-streptavidine horseradish peroxidase (SA-HRP, Sigma). After 30 min, the samples were washed and the specific labelling was visualized using diaminobenzidine (DAB, Sigma) as substrate. Tissue sections taken in the absence of primary antibody were included as negative controls.

Analysis of N-Glycosylation of the Antibodies Using LC-ESIMS

Anti-IgE rat IgG antibodies (R35-72 and R35-92 by BD Biosciences, eBRG1 and eBR2 by eBiosciences, LO-ME2 by Invitrogen) were denatured (6 M urea) and reduced (75 mM DTT, 50° C., 15 min) before analysis by LC-ESI MS. Analysis of the reduced heavy chains by ESI MS was performed after chromatographic separation of the light chains and heavy chains. The IgGs were also subjected to LC-ESIMS after deglycosylation (PNGase F treatment, Glycoprofile II, Sigma) or enzymatic removal of sialic acid (sialidase Au, QA Bio) following the manufacturer's instructions. In brief, about 2 μg of reduced antibody were injected into an Acquity $C_4$, 10 cm×2.1 mm, 1.7 μm (BEH300, Waters) thermostated at 80° C. and connected to an RS-HPLC system (Dionex). A gradient of $CH_3CN$ (with 0.1% v/v formic acid) was set up with a flow rate of 400 μl/min to ensure proper UV detection at 210 nm. A Qq-TOF mass spectrometer (Maxis, Bruker) was connected to the RS-HPLC for correct mass measurement and was operated under positive ionization mode. Deconvolution of the mass spectrum was conducted using the MaxEnt algorithm (Waters Corp.) and the following parameters: 45000-55000 Da, auto-spacing of data points, resolution 40000. Therefore the masses of the intact desialylated and deglycosylated heavy chains were obtained so as to identify the glycosylation profiles.

Results

Identification of the Cells Carrying the Fc Receptors of IgGs in the Tongue Tissues of Naive and OVA-Sensitized BALB/c Mice In order to determine the tissue distribution of the Fc receptor of the IgGs, the inventors analyzed the tongue tissues of naive and OVA-sensitized BALB/c mice by immunohistology using specific antibodies, i.e. CD16/CD32 and SIGN-R1. CD16/CD32 was detected at the mucosal/sub-mucosal interface both at the ventral and dorsal tissue sites of the tongue and in the muscular region, both in the naive mice and the OVA-sensitized mice. On the other hand, SIGN-R1 was only detected in the muscular tissue (both in naive mice and OVA-sensitized mice), far from the sublingual administration site.

Analysis of N-Glycosylation of the Antibodies by LC-ESIMS

The IgGs were denatured and reduced before analysis by LC-ESIMS of the intact, desialylated and deglycosylated heavy chains, in order to identify their respective glycosylation profiles.

The different oligosaccharidic structures were determined by LC-ESIMS, both before and after enzymatic digestion (i.e. deglycosylation and removal of sialic acid). The R35-92 antibody displayed structural heterogeneity of the glycoforms of heavy chains, with the successive addition of different monosaccharides to the N-linked oligosaccharide. The mass spectrum of the deglycosylated R35-92 antibody shows the weight (49075 Da) of the polypeptide of the heavy chain, whilst the mass spectrum of the native heavy chain shows a weight increase of 1298 Da corresponding to the addition of a non-fucosylated, non-galactosylated, non-sialylated, biantennary structure (observed weight 50373 Da). Biantennary, sialylated, galactosylated and fucosylated glycans were also evidenced. The treatment with sialidase confirmed the presence of both mono and bisialylated, biantennary, fucosylated structures. Similar experiments were performed on each antibody. The results are summarized in Table 2 below.

TABLE 2

Summary of the characterization of N-glycosylation of the heavy chains

| Clone | Isotype | Activity | Sialylation | Fucosylation |
|---|---|---|---|---|
| R35-72 | $IgG_1$ | + | ND | 40% |
| R35-92 | $IgG_1$ | + | 30% | 50% |
| eBRG1 | $IgG_1$ | + | ND | ND |
| eBRG2 | $IgG_2a$ | − | ND | 100% |
| LO-ME* | $IgG_2a$ | − | ND | 50% |

ND: non-detected
*the LO-ME antibody shows an unusual mass spectrum profile

According to RS-HPLC followed by high resolution and high precision ESIMS analysis, all the tested anti-IgE monoclonal rat IgG antibodies (R35-72, R35-92, eBRG1, eBRG2 and LO-ME2) display N-glycosylated heavy chains. Regular oligosaccharide structures, of which the majority are biantennary and non-galactosylated, were observed. Glycosylation differed between antibodies' since significant sialylation (about 30%) was only observed in sample R35-92. In addition, the absence of core fucose (sample eBRG1) and partial or total fucosylation (samples R35-92 and eBRG2 respectively) were also evidenced. Therefore, neither sialylation nor fucosylation play a critical role in tolerance-inducing activity.

EXAMPLE 4

This study shows the identification of the receptors of the Fc part of $IgG_1$ in human buccal tissues.

The anti-CD32 antibodies (clone AT10, ref ab41899, Abcam) recognize the family CD32 inhibitor receptors.

The presence of cells expressing CD32 was detected by immuno-histochemistry at the mucosal/sub-mucosal junction of human gum tissue.

The inventors observed moderate to pronounced intensity labelling of immune cells in very high quantities in the papillary corium (buccal side).

The anti-CD16 antibodies (clone 2H7, ref ab74512, Abcam) recognize the family of CD16 activator receptors.

The presence of cells expressing CD16 was detected by immuno-histochemistry at the mucosal/sub-mucosal junction of human gum tissue.

The inventors observed moderate intensity labelling of immune cells in small quantities in the papillary corium (buccal side).

The inventors have therefore shown that at human gums level, the balance between the CD16 activator receptors and CD32 receptors (which comprise inhibitor receptors) leaned in favour of the latter. They are detected in greater quantity at the papillary corium. As a result, the presence of a larger number of CD32 receptors is in favour of the use of CD32 ligands, and in particular of $IgG_1$ immunoglobulin, via mucosal route, in particular via sublingual route, in human for the treatment of inflammatory diseases and manifestations.

The invention claimed is:

1. A method of treatment of a type 1 hypersensitivity in a subject, comprising administering to a subject in need thereof a therapeutically effective amount of anti-IgE antibody having the capacity of binding the IgEs fixed to the receptors on the surface of a mastocyte or basophile without dissociating said IgEs from their receptors, the anti-IgE antibody being administered via mucosal route.

2. The method according to claim 1, the antibody having the capacity of bridging IgEs fixed to the receptors on the surface of a mastocyte or basophile.

3. The method according to claim 1, the antibody recognizing a part of the IgE not involved in the fixing of the IgE to its receptor on the mastocyte or basophile.

4. The method according claim 1, wherein in the sign of the type 1 hypersensitivity is systemic anaphylaxis, localized anaphylaxis, allergic rhinitis, asthma, atopical dermatitis, conjunctivitis, eczema, mastocytosis induced by anaphylactic shock, an allergic sign associated with parasitosis.

\* \* \* \* \*